United States Patent
Stadler et al.

(10) Patent No.: US 7,062,322 B2
(45) Date of Patent: Jun. 13, 2006

(54) RHYTHM-BASED TRANSITION TO DISCRIMINATORY ARRHYTHMIA CLASSIFICATION

(75) Inventors: Robert W. Stadler, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 369 days.

(21) Appl. No.: 10/023,234

(22) Filed: Dec. 18, 2001

(65) Prior Publication Data

US 2003/0114888 A1 Jun. 19, 2003

(51) Int. Cl.
*A61N 1/365* (2006.01)

(52) U.S. Cl. ........................................................ 607/9
(58) Field of Classification Search ................ 607/4–9, 607/14, 15, 30, 25, 32; 600/508–515, 521
See application file for complete search history.

(56) References Cited

U.S. PATENT DOCUMENTS

| | | | | |
|---|---|---|---|---|
| 4,998,974 | A | * | 3/1991 | Aker ............................ 607/4 |
| 5,063,928 | A | | 11/1991 | Grevis et al. |
| 5,086,772 | A | * | 2/1992 | Larnard et al. ................ 607/4 |
| 5,191,884 | A | * | 3/1993 | Gilli et al. ..................... 607/5 |
| 5,370,667 | A | | 12/1994 | Alt |
| 5,403,352 | A | | 4/1995 | Rossing |
| 5,403,355 | A | | 4/1995 | Alt |
| 5,755,736 | A | | 5/1998 | Gillberg et al. |
| 6,052,620 | A | | 4/2000 | Gillberg et al. |
| 6,169,923 | B1 | | 1/2001 | Kroll |
| 6,233,487 | B1 | | 5/2001 | Mika et al. |
| 6,272,377 | B1 | | 8/2001 | Sweeney et al. |
| 2002/0128562 | A1 | * | 9/2002 | Bocek et al. ................ 600/508 |
| 2004/0249420 | A1 | * | 12/2004 | Olson et al. ................... 607/9 |

FOREIGN PATENT DOCUMENTS

EP 1 112 756 A2 4/2001

OTHER PUBLICATIONS

"Model 3510 Programmer with Model 3307-2.3 Software for Photon and Photon Micro Implantable Cardioverter Defibrillator," Photon DR, Chapter 3 of the Reference Manual.
Advertisement from Journal "PACE", PARAD™ Algorithm Diagnosis Tree.
Photon Algorithm Flowchart.

* cited by examiner

*Primary Examiner*—George Manuel
(74) *Attorney, Agent, or Firm*—Daniel G. Chapik; Girma Wolde-Michael (57) ABSTRACT

In a medical device that monitors and/or treats ventricular arrhythmia, the invention provides for a "normal" processing mode of operation and a "guarded" processing mode of operation. The transition between the two modes is a function of cardiac rhythm. Benign rhythms are processed in the normal processing mode and non-benign rhythms are processed in the guarded processing mode. In normal processing mode, the device performs functions that are not computationally demanding, but in guarded processing mode, the device performs the computationally demanding operations that classify arrhythmias. If therapy is deemed necessary, the device may provide the therapy in guarded processing mode.

26 Claims, 7 Drawing Sheets

RHYTHM-BASED TRANSITION TO DISCRIMINATORY ARRHYTHMIA CLASSIFICATION

TECHNICAL FIELD

The invention relates to processing of cardiac signals, and more particularly, to monitoring of cardiac arrhythmias.

BACKGROUND

Many implanted cardiac devices monitor the electrical activity of the heart for tachyarrhythmias. When the implanted device senses a possible tachyarrhythmia, a processor in the implanted device performs computations to classify the tachyarrhythmia. Classifying the tachyarrhythmia may include identifying or discriminating the form of tachyarrhythmia, such as non-sustained ventricular tachycardia, sustained ventricular tachycardia or dual-chamber tachycardia. Some forms of tachyarrhythmia are life-threatening, while other forms of tachyarrhythmia pose little risk to the life of the patient. When the implanted device identifies a life-threatening tachyarrhythmia, the implanted device may provide therapy to the heart, such as anti-tachycardia pacing, cardioversion or defibrillation.

Classifying the tachyarrhythmia involves applying powerful discriminatory algorithms, and consequently involves extensive computation by the processor. Classification computations take more time than many other processor operations, and therefore consume more energy than many other processor operations. As a result, classification computations generally act as a greater drain on the battery of the implanted device, in comparison to other processor operations.

As discriminatory algorithms to classify tachyarrhythmias have become more sophisticated, the computation effort associated with classification has increased. More sophisticated classification algorithms require more computation and drain more energy from the battery.

To prolong battery life, the implanted device performs classification computations in a defined set of circumstances. When the patient's heart rate is normal, for example, the processor does not need to classify any arrhythmia, and so the processor avoids performing energy-demanding classification computations. The processor may operate in a low-energy state when the patient's heart rate is normal, performing minimal, short-duration computations with each cardiac cycle, thereby consuming less energy. The processor departs from the low-energy state and makes a transition to a high-energy computational state when conditions exist that call for the energy-demanding computations.

In a conventional implanted cardiac device, the transition from the low-energy state to the high-energy computational state is based upon heart rate. In other words, the device monitors the rate of activation of the ventricles and/or atria, and makes a transition to the high-energy computational state when the rate exceeds a predetermined threshold for a predetermined duration. The threshold rate and duration are typically set by the patient's physician. Equivalently, the physician may set a threshold time interval between activations, which is inversely proportional to the threshold rate. One such threshold interval is defined as the tachycardia detection interval (TDI). The threshold duration may be set as a programmed number of intervals to detection (NID). Rhythms with intervals less than the TDI for at least NID consecutive beats trigger entry to the high-energy computational state. The discussion that follows will refer to intervals and to rates, and is equally applicable to both.

With conventional implanted cardiac devices, when the patient experiences a tachyarrhythmia with intervals greater than the TDI, the device does not enter the high-energy computational state and consequently does not classify the arrhythmia. The device could fail to classify a tachyarrhythmia, such as ventricular tachycardia, if the intervals are greater than the TDI. Ventricular tachycardia may be a serious, and possibly life-threatening, event.

As a practical matter, tachyarrhythmia classification is a prerequisite to effective treatment. When a tachyarrhythmia is not classified, the device typically will not provide therapy to treat the tachyarrhythmia. Unfortunately, some tachyarrhythmias that fail to cross the threshold can be life-threatening and yet may go untreated.

The patient's physician may choose to detect and treat slower tachyarrhythmias by setting a more easily crossed threshold. Not all slower tachyarrhythmias are dangerous to the patient, however, and setting a more easily crossed threshold may cause the processor to spend more time in the high-energy computational state performing classification computations. Increased time in the high-energy computational state in turn results in greater demand on the batteries in the device. The implanted device may therefore spend considerable energy to classify rhythms, many of which are not dangerous.

As a result, a rate-based transition may comprise unattractive trade-offs. Setting a TDI too high may lead to wasted computational effort that unnecessarily drains the batteries in the implanted device. The relationship between the TDI and the resulting computational demand is approximately exponential, so increasing the TDI by a small amount may result in a significant increase in computational activity and battery drain. Setting the TDI too low, however, may result in potentially dangerous tachyarrhythmias being unclassified and untreated.

SUMMARY

In general, the invention provides for establishing a "normal" processing mode of operation and a "guarded" processing mode of operation in the implanted medical device, and makes a transition between the two modes as a function of cardiac rhythm. In normal processing mode, the device performs a comparatively simple rhythm analysis that is not computationally demanding and consumes relatively little energy. The purpose of the simple rhythm analysis is to attempt to determine whether the rhythm is one of a set of benign rhythms. Examples of benign rhythms may include normal sinus rhythm, sinus tachycardia, atrial fibrillation, atrial flutter, 1:1 supraventricular tachycardia, predominantly paced rhythm, bigeminy, and non-sustained ectopy. A determination that the rhythm is benign maintains operation in normal processing mode and thus inhibits application of the highly discriminatory but computationally demanding arrhythmia classification algorithms.

Departure of the current rhythm from the set of benign rhythms forces a transition from normal processing mode into guarded processing mode. In guarded processing mode, the highly discriminatory but computationally demanding arrhythmia classification is activated and therapy may be delivered if appropriate. In some circumstances, classification of the arrhythmia may be followed by monitoring, i.e., storing information about the arrhythmia without delivery of therapy. When a benign rhythm returns, or when the arrhythmia terminates in response to therapy, the device returns to normal processing mode.

Although the transition between normal and guarded processing modes is a function of cardiac rhythm, the invention accommodates, but does not require, an additional rate-based transition. In other words, the device may make a transition to guarded processing mode when a series of intervals falls below a programmed TDI, but the rate-based transition is not essential to the invention.

In one embodiment, the invention provides a method comprising operating a processor in a first computational state and operating the processor in a second computational state in response to a non-benign heart rhythm. In the second computational state, the method includes executing discriminatory arrhythmia classification algorithms. The first computational state is the low-energy normal processing state, and the second computational state is the high-energy computational guarded processing state. The processor enters the second computational state when, for example, there is evidence of dual tachycardia or when there is evidence of atrial fibrillation, atrial flutter or sinus tachycardia, with atrioventricular dissociation and R-R interval stability.

In another embodiment, the invention provides a method comprising sensing a cardiac rhythm, operating a processor in a first computational state when the sensed cardiac rhythm is a benign rhythm and operating the processor in a second computational state when the sensed cardiac rhythm is a non-benign rhythm. Benign rhythms include, but are not limited to, normal sinus rhythm, sinus tachycardia, atrial fibrillation, atrial flutter, 1:1 supraventricular tachycardia, a paced rhythm, bigeminy and non-sustained ectopy. Benign rhythms may be identified with little computational effort. When a rhythm is non-benign, the processor executes discriminatory arrhythmia classification algorithms to classify the heart rhythm.

The invention may be embodied in a computer-readable medium with instructions that cause a programmable processor to carry out the methods. The invention may further be embodied as a device that can carry out the methods. The device may comprise a sensor proximal to a ventricle of a heart and a processor that operates in one of a first computational state and a second computational state as a function of a cardiac rhythm sensed via the sensor without regard to heart rate. The processor executes discriminatory arrhythmia classification algorithms when the processor is in the second computational state.

The invention offers one or more advantages. With a rhythm-based transition, the invention monitors and/or treats tachyarrhythmias at all rates, not merely those rates that have intervals less than a pre-selected TDI. In some embodiments, it is unnecessary for a physician to specify a TDI threshold. The comparatively simple rhythm analysis performed in normal processing mode evaluates rhythms at all rates. The device makes a transition to guarded processing mode when the rhythm may be dangerous, regardless of the rate.

Although the rhythm-based analysis performed in normal processing mode is a more advanced analysis than determining whether the rate exceeds a predetermined threshold, the rhythm analysis in normal processing mode is far less computationally demanding than arrhythmia classification in guarded processing mode. The rhythm-based analysis performed in normal processing mode identifies those rhythms that are more likely to need the more sophisticated classification computations. By performing a rhythm-based analysis in normal processing mode, the device conserves computational resources by making a transition into the guarded processing state when classification is likely to be needed. Because there is less likelihood of unnecessary classification, there is less unnecessary drain on the batteries in the device.

In addition, various embodiments of the invention may be especially advantageous for certain patients. A device that monitors bradycardia, for example, may include tachyarrhythmia monitoring capability but no ventricular therapy capability. In another embodiment, a device that provides tachyarrhythmia therapy and pacing may benefit from separate tachyarrhythmia monitoring and therapy zones.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
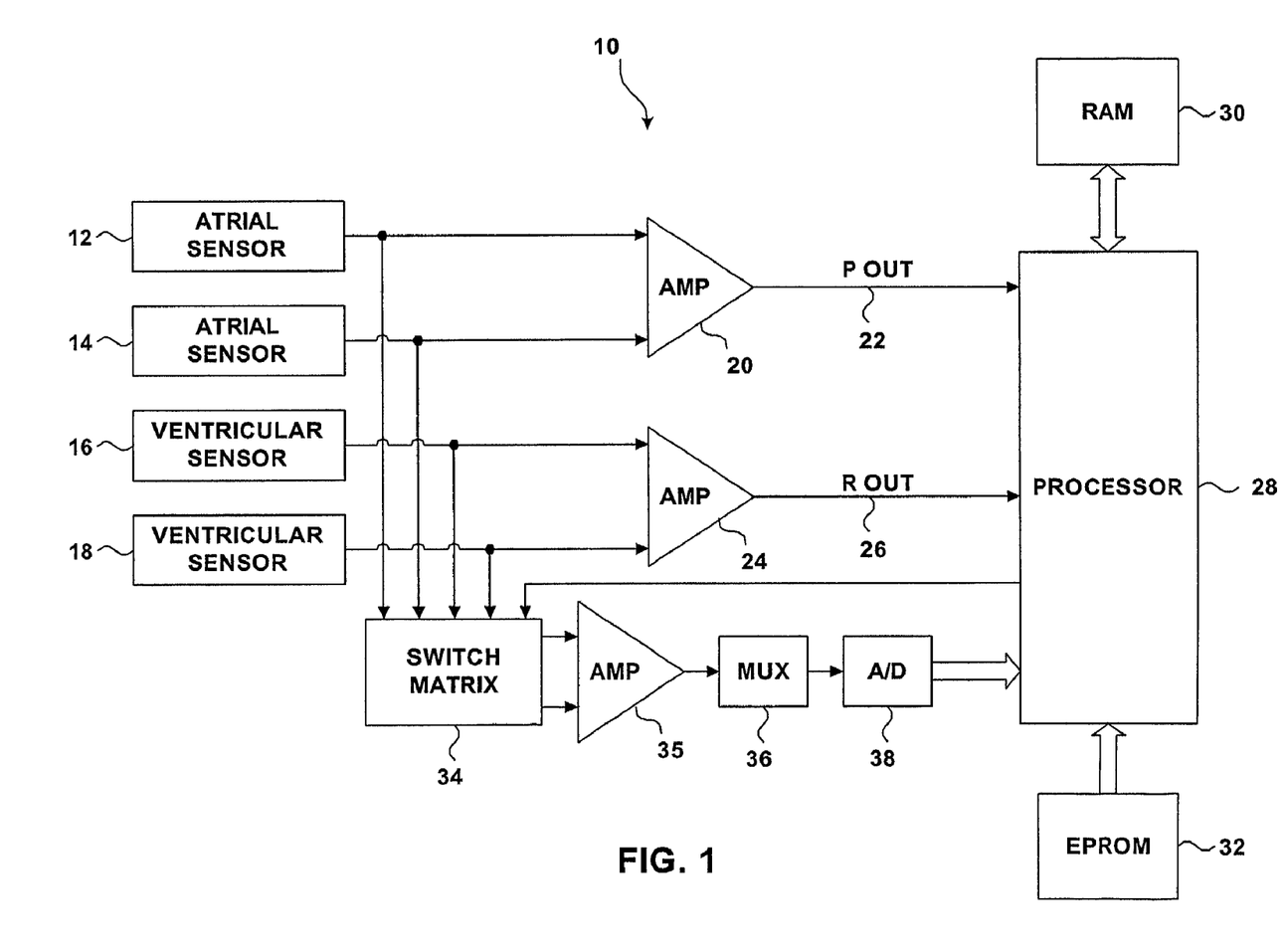
FIG. 1 is a block diagram illustrating an exemplary system implementing the invention.

FIG. 1 is a block diagram illustrating an exemplary system 10 implementing the invention. System 10 is a part of an implanted medical device such as a pacemaker or a pacemaker-defibrillator. System 10 may also be included in an arrhythmia monitor that gathers data but does not provide any therapy to the patient.

System 10 receives atrial signals via atrial sensors 12, 14, and receives ventricular signals via ventricular sensors 16, 18. Atrial sensors 12, 14 and ventricular sensors 16, 18 may be, for example, pace/sense electrodes proximal to the right atrium and right ventricle, respectively. A sense amplifier 20 receives electrical signals from atrial sensors 12, 14, amplifies and filters the signals, and senses whether the signals show an atrial activation. As used herein, an activation is defined as an electrical excitation that propagates along the cardiac tissue. Amplifier 20 may sense an atrial activation by techniques such as comparing the signal to a sense threshold.

When amplifier 20 senses an atrial activation, amplifier 20 generates a digital signal on P-out line 22.

Similarly, a sense amplifier 24 receives signals from ventricular sensors 16, 18, amplifies and filters the signals, and senses whether the signals show a ventricular activation. When amplifier 24 senses a ventricular activation, amplifier 24 generates a digital signal on R-out line 26.

The invention may be practiced with systems other than system 10. For example, the invention may be practiced in an implantable arrhythmia monitor that receives a single electrocardiogram (ECG) signal. A P-wave indicative of atrial activation may be discriminated from the ECG signal, causing generation of a digital signal on P-out line 22. Similarly, an R-wave indicative of ventricular activation may be discriminated from the ECG signal, causing generation of a digital signal on R-out line 26.

Processor 28 receives signals from P-out line 22 and R-out line 26. Processor 28 processes the signals in a "normal" processing mode or a "guarded" processing mode. Processor 28 performs highly discriminatory but computationally demanding arrhythmia classification in the guarded processing mode, but not in the normal processing mode. In general, processor 28 determines whether the signals indicate a benign rhythm. Benign rhythms are handled in normal processing mode. Rhythms that are not benign are classified in the guarded processing mode.

In one implementation, "benign" rhythms include, for example, normal sinus rhythm (NSR), atrial fibrillation (AF), atrial flutter (AFL) and 1:1 supraventricular tachycardia (SVT). In an embodiment that includes a pacemaker, a paced rhythm is deemed to be benign. Bigeminy and non-sustained ectopy may also be deemed to be benign. Each of these conditions may be identified with a minimal amount of computational effort, and it is not necessary to enter into guarded processing mode to classify these conditions. Each of these conditions may be deemed to be non-life-threatening.

Some rhythms may be benign at high intervals, but not benign at low intervals. For example, episodes such as 1:1 SVT or sinus tachycardia (ST), may be deemed benign above an interval of 300 milliseconds (i.e., less than 200 beats per minute), and not benign below an interval of 300 milliseconds. The interval that separates benign from non-benign may therefore be designated by a threshold, such as the TDI selected by the physician.

When processor 28 determines the rhythm is not benign, processor 28 enters the guarded processing mode. In the guarded processing mode, an arrhythmia can be carefully classified, monitored, and if the circumstances warrant, treated with therapy. Classification may involve an analysis of the waveform sensed by ventricular sensors 16, 18, in addition to the timing of recent P-waves on P-out line 22 and the timing of recent R-waves on R-out line 26. Analysis of waveforms generally involves converting analog electrical signals to digital signals for analysis.

Switch matrix 34 selects which of the available sensors are coupled to wide band (0.5 to 200 Hz) amplifier 35 for use in digital signal analysis. Processor 28 controls selection of sensors. Signals from the selected sensors are provided to multiplexer 36 and are converted to multi-bit digital signals by analog-to-digital (A/D) converter 38. The digital signals, which may include digital atrial waveforms, digital ventricular waveforms, or both, may be analyzed by processor 28. Classification may include computationally demanding techniques such as morphological analysis. Morphological analysis may include, for example, wavelet analysis, Fourier analysis or template matching. As a result, the guarded processing mode is a more computationally demanding and energy-demanding mode than the normal processing mode.

Discriminatory classification algorithms may be encoded as a sequence of instructions stored in memory components such as random access memory (RAM) 30 and/or erasable programmable read-only memory (EPROM) 32. Processor 28 may load the instructions from RAM 30 or EPROM 32 when classifying an arrhythmia. RAM 30 or EPROM 32 may also store algorithms as sequences of instructions for determining whether system 10 should assume a normal processing mode or a guarded processing mode. These algorithms, which will be described in more detail below, are less computationally demanding and consume less battery power than the arrhythmia classification algorithms in guarded processing mode.

In addition, data pertaining to the condition and/or treatment of the patient may be stored in RAM 30, such as the number of atrial or ventricular episodes experienced, and the therapy provided in response to an episode.

Figure 2:
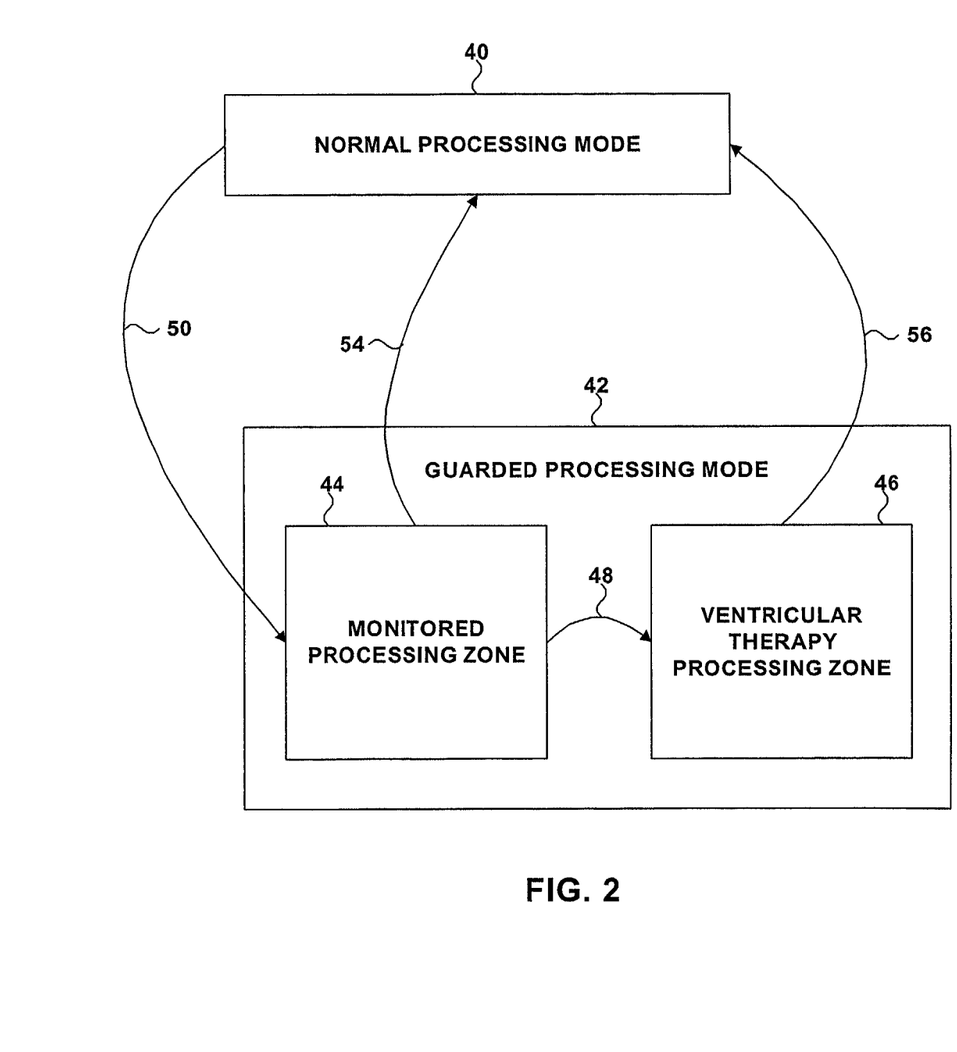
FIG. 2 is a state diagram illustrating the normal processing mode and the guarded processing mode, as well as a monitored processing zone and a ventricular therapy processing zone in the guarded processing mode.

FIG. 2 is a state diagram of an exemplary embodiment of the invention. Processor 28 may operate in a normal processing mode 40 and a guarded processing mode 42. In the embodiment depicted in FIG. 2, guarded processing mode 42 includes a monitored processing zone 44 and a ventricular therapy processing zone 46. In both zones 44, 46, processor 28 performs computationally demanding classification operations. In monitored processing zone 44, the arrhythmia is classified and monitored. In ventricular therapy processing zone 46, the arrhythmia may be classified, monitored and treated with therapy. "Monitoring" may include storing information about the arrhythmia in random access memory 30 for later retrieval by the patient's physician.

In some circumstances, the episode terminates on its own, a benign rhythm returns, and processor makes a transition 54 back to normal mode 40. In other circumstances, therapy for a classified arrhythmia may be indicated, and processor 28 makes a transition 48 to ventricular therapy processing zone 46. The circumstances that may warrant this transition 48 will be discussed below.

This exemplary embodiment of the invention focuses upon ventricular arrhythmias, which are usually more serious than atrial arrhythmias. In this exemplary embodiment, many atrial arrhythmias are deemed benign and will not cause processor 28 to make a transition 50 from normal processing mode 40 to guarded processing mode 42. Accordingly, ventricular therapy processing zone 46 focuses upon ventricular, rather than atrial, therapies. Some forms of atrial arrhythmia, such as supraventricular tachycardia with 1:1 atrioventricular (AV) conduction, however, may not be considered benign and will cause processor 28 to make a transition to guarded processing mode 42.

Moreover, the invention does not exclude therapy for atrial arrhythmias that are considered benign. On the contrary, the invention may be practiced in conjunction with techniques for treating atrial arrhythmias. For example, detection of and therapy for atrial episodes, such as atrial arrhythmias with greater than 1:1 AV conduction, may be handled independently of the detection, monitoring and treatment of ventricular episodes. Processor 28 may perform detection, monitoring and treatment of atrial episodes whether in normal processing mode 40 or monitored processing zone 44 of guarded processing mode 42. When processor 28 is in ventricular therapy processing zone 46 of guarded processing mode 42, however, atrial therapy may be suspended, because ventricular therapy takes precedence.

While in ventricular therapy processing zone 46, processor 28 may initiate administration of therapy. Processor 28 remains in ventricular therapy processing zone 46 as long as the arrhythmia is present. The arrhythmia may terminate following administration of therapy, but processor 28 may remain in ventricular therapy processing zone 46 for a short time to confirm termination of the episode. When the arrhythmia terminates, processor 28 makes a transition 56 from guarded processing mode 42 to normal processing mode 40.

Figure 3:
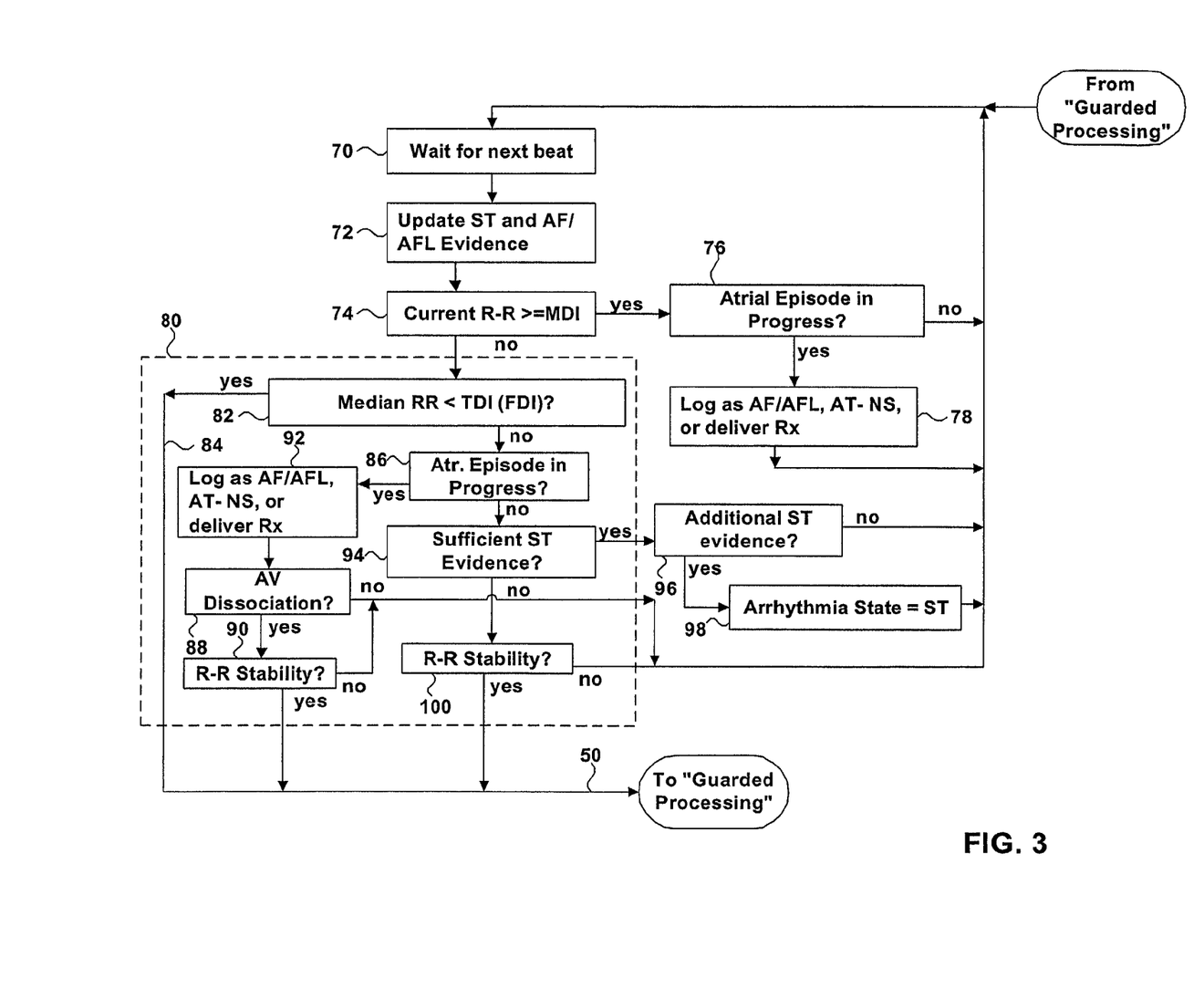
FIG. 3 is a flow diagram illustrating processing in the normal processing mode.

FIG. 3 is a flow diagram illustrating an example of computational analysis by processor 28 in normal processing mode 40. The analysis is less computationally demanding than the computations in guarded processing mode 42. Following electrical activation of the ventricles (70), processor 28 computes the intervals between the R-wave of the current beat and the R-wave of the previous beat (the R-R interval). Based on the timing of P-waves and R-waves in the most recent R-R interval, processor 28 updates the current evidence of ST, AF and AFL (72).

Although the evidence is updated on a beat-by-beat basis, the evidence accumulates over time. Updating evidence may include, for example, incrementing or decrementing counters as a function of atrial and ventricular pattern information, as disclosed by the timing of the P-waves and the R-waves. The counters indicate whether the patient is experiencing an atrial episode. When there is moderate evidence of AF or AFL, for example, processor 28 recognizes an "atrial episode in progress" and may respond by setting a flag so indicating. Whether the flag is set may be a factor in determining whether to transition to guarded processing mode 42 (86). Because evidence of AF and AFL is continually accumulated, processor 28 recognizes the onset of an atrial episode quickly. Incrementing or decrementing counters is an exemplary technique for updating evidence of ST, AF and AFL (72), and the invention is not limited to that technique.

The R-R interval may be compared to a monitor detection interval (MDI) (74), which represents a maximum interval of interest. For example, an interval above an MDI of 600 milliseconds (i.e., a heart rate less than 100 beats per minute) may be deemed to be benign. As noted above, however, the invention may be practiced at all heart rates, i.e., without the need for an MDI, and may be practiced in conjunction with techniques for treating atrial arrhythmias independently of the transition between processing states. In the case of AF, AFL or non-sustained atrial tachycardia (AT-NS) (76), an R-R interval above the MDI may still result in recordation, analysis and therapy (Rx) (78) of the atrial condition. Processor 28 remains in normal processing mode 40 and does not transition to guarded processing mode 42.

When the R-R interval is less than the MDI, processor 28 performs an analysis to determine whether to remain in normal processing mode 40 or whether to transition to guarded processing mode 42 (80). Processor 28 may transition to guarded processing mode 42 along any of three separate paths.

In the first path, processor 28 may transition to guarded processing mode 42 if the ventricular activations occur too quickly (82), indicating a rhythm that is likely too fast to allow adequate cardiac output or perfusion of cardiac tissue during diastole. The threshold for this transition may be the TDI or fibrillation detection interval (FDI) set by the physician. The median R-R interval is a function of several interval measurements, including the current R-R interval and previous R-R intervals. The median R-R intervals may be calculated over, for example, seven to twelve beats. When the median R-R interval is less than the TDI (or FDI), processor 28 transitions to guarded processing mode 42 via path 84. A single R-R interval shorter than the TDI (or FDI) will ordinarily not cause processor 28 to transition to guarded processing mode 42.

In many cases, the patient's physician may be interested in monitoring and treating slower tachyarrhythmias as well. The second and third paths to guarded processing are concerned with slower tachyarrhythmias.

The second path is concerned with dual tachycardia, in which the atria and ventricles are beating rapidly, independently, and out of phase. When an atrial episode is in progress (86), with evidence of AV dissociation (88) and sufficient stability in the R-R interval (90), dual tachycardia is a possibility. Dual tachycardia is not a benign rhythm, and processor 28 makes a transition to guarded processing mode 42. Atrial monitoring and therapy may also be provided (92).

The third path is concerned with other arrhythmias. Sinus tachycardia is a benign rhythm, and when there is sufficient evidence of sinus tachycardia (94), then some additional processing may be performed to confirm classification of the condition as sinus tachycardia (96, 98). Some medical devices may not be concerned with storing information about ST, and may not perform the additional processing (96, 98). Whether or not additional processing (96, 98) is performed, processor 28 remains in normal processing mode 40. If there is insufficient evidence of ST, processor 28 checks the rhythm for R-R stability (100). Lack of sufficient R-R stability (100) suggests bigeminy or non-sustained ectopy, which are classified as benign rhythms and likewise do not lead to guarded processing mode 42.

The analysis that determines whether to transition to guarded processing mode 42 (80) uses relatively little computational effort. When a rhythm satisfies the tests of one of the three paths in the analysis (80), processor 28 makes the transition to guarded processing mode 42.

Figure 4:
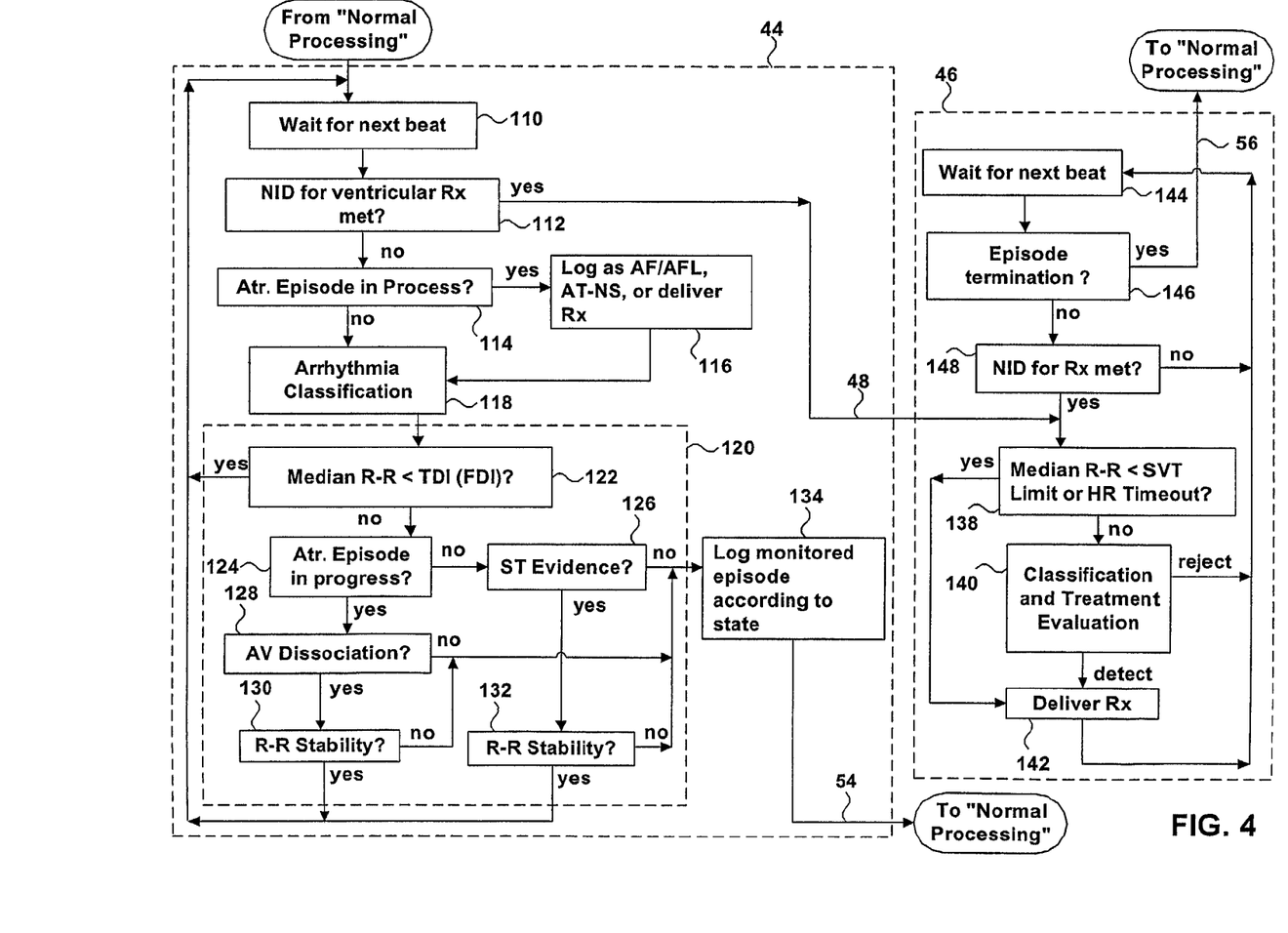
FIG. 4 is a flow diagram illustrating processing in the guarded processing mode shown in FIG. 2.

FIG. 4 is a flow diagram illustrating an example of computational analysis by processor 28 in guarded processing mode 42. Guarded processing mode 42 includes monitored processing zone 44 and ventricular therapy processing zone 46. In the embodiment depicted in FIG. 4, processor 28 enters monitored processing zone 44 from normal processing mode 40.

On the ventricular electrical activation after entering monitored processing zone 44 (110), processor 28 determines whether the number of consecutive R-R intervals below the programmed TDI (or FDI) exceeds a programmed threshold duration, called the number of intervals to detect (NID) (112). The NID is programmed by the physician. The purpose of the NID is to avoid treatment of isolated or short-lived arrhythmias. When the number of intervals of non-benign rhythm exceeds the NID threshold, therapy may be indicated, and processor 28 makes transition 48 to ventricular therapy processing zone 46. When the number of intervals of non-benign rhythm is less than the NID threshold, processor 28 remains in monitored processing zone 44.

Processor 28 senses whether an atrial episode is in progress (114). As noted above, AF and AFL may be detected by evaluating the timing of P-waves and R-waves, and this evidence is accumulated over time. When additional evidence of AF or AFL is obtained, recordation, analysis and/or therapy (116) may be administered. Notably, detection, analysis and treatment of atrial episodes may be handled in normal processing mode 40 (76, 78, 86, 92) and in monitored processing zone 44 of guarded processing mode 42 (114, 116). Consequently, detection, monitoring and treatment of atrial episodes is often independent of the detection, monitoring and treatment of ventricular episodes.

Processor 28 classifies the arrhythmia (118) using computationally demanding discriminatory techniques such as morphological analysis and/or algorithms that operate on P- and R-wave interval information. Morphological analysis may include techniques such as template matching, wavelet analysis, Fourier analysis. Classification (118) requires more time and therefore more energy than analysis performed in normal processing mode 40. In addition to identifying the arrhythmia, classification (118) may also include recording data about the arrhythmia for retrieval by the physician. In this way, processor 28 monitors the arrhythmia, but does not provide therapy.

Following classification (118), processor 28 performs an analysis to determine whether to remain in guarded processing mode 42 or whether to transition to normal processing mode 40 (120). This analysis is the complement to analysis (80) in normal processing mode 40. Processor 28 may remain in guarded processing mode 42 via any of three separate paths.

In the first path, processor 28 may remain in guarded processing mode 42 if the ventricular activations occur too quickly (122). The analysis (122) is the same as the analysis (82) in normal processing mode 40.

Processor 28 may remain in guarded processing mode 42 when dual tachycardia is suspected. As in normal processing mode 40 (86, 88, 90), this second path involves determining whether there is an atrial episode in progress (124), with evidence of AV dissociation (128) and sufficient R-R stability (130).

Like the third path in normal processing mode 40 (94, 100), the third path in monitored processing zone 44 (126, 132) is concerned with other arrhythmias. Arrhythmias such as ST, bigeminy or non-sustained ectopy will not cause processor 28 to remain in guarded processing mode 42.

When a rhythm does not adhere to any of the three paths, processor 28 may conclude diagnostic storage of the event (134) and may consider any currently monitored non-benign rhythm as terminated. Processor 28 returns to normal processing mode 40 (54). A rhythm that does adhere to one of the three paths, however, causes processor 28 to remain in monitored processing zone 44. Processor 28 waits for the next ventricular activation (110) and processes this beat. Notably, processor 28 performs analysis in monitored processing zone 44 on a beat-to-beat basis, and when the condition that caused processor 28 to enter monitored processing zone 44 disappears, processor 28 quickly makes a transition 54 to normal processing mode 40.

When processor 28 determines that the NID threshold has been exceeded (112), processor 28 makes a transition 48 to ventricular therapy processing zone 46. Processor 28 may administer therapy (142) depending upon whether the rhythm maintains classification as a non-VT or VF rhythm (140) and whether the median R-R interval is less than the SVT limit or a high rate (HR) timeout occurs (138). The SVT limit and HR timeout are "safety net" features that prevent withholding of therapy for urgent conditions pending classification. When the R-R median is less than a programmed SVT limit parameter, then the rhythm is too fast to be an SVT, and therapy is delivered promptly without waiting for classification (142). Similarly, when the rate has been very high for an extended period of time, such that the rhythm is more likely a ventricular tachycardia than an SVT, the programmable HR timeout may trigger prompt delivery of therapy without waiting for classification (142). In cases in which the condition is not urgent, processor 28 may further classify the arrhythmia and evaluate whether a treatable rhythm is detected (140). Following classification (140), therapy may be rejected when the rhythm is highly unlikely to be a ventricular tachycardia of ventricular fibrillation. Otherwise, therapy is delivered (142).

Whether or not therapy is provided, processor 28 remains in ventricular therapy processing zone 46. Processor 28 receives data for each beat (144) and determines whether the ventricular episode has terminated (146). One test for episode termination may be whether a predetermined number of beats are above a threshold interval. For example, if eight beats in a row are slower than the TDI, processor 28 may determine that the episode has terminated, and make a transition (56) to normal processing mode 40. The number of slow beats may be, but need not be, the same as the number of intervals in the NID threshold.

In some cases, there may be some slow beats, but fewer than the number needed to cause processor 28 to make a transition (56) to normal processing mode 40. Processor 28 remains in ventricular therapy processing zone 46, in case the arrhythmia returns. A single R-R interval greater than the TDI clears the NID counter. Processor 28 determines whether the NID threshold has been exceeded (148), and if so, additional therapy may be provided (142).

Unlike monitored processing zone 44, ventricular therapy processing zone 46 does not include atrial therapy. In ventricular therapy processing zone 46, processor 29 suspends atrial therapy, because ventricular therapy takes precedence.

The embodiments depicted in FIGS. 3 and 4 are exemplary and may be modified for particular implantable medical devices. An implantable cardioverter defibrillator (ICD), for example, may include additional techniques in normal processing mode 40 or in guarded processing mode 42. An ICD may consider additional event counters or other criteria not shown in FIGS. 3 or 4. A device that monitors bradycardia may not be equipped to treat tachycardia, and consequently a bradycardia device could omit a ventricular therapy processing zone 46 altogether. In other words, a bradycardia device may classify arrhythmias without being able to treat the arrhythmias.

The exemplary embodiments of FIGS. 3 and 4 accommodate a physician-specified interval such as a TDI or FDI. As will be shown below, the invention need not include a physician-programmed interval. In other words, the invention may transition between normal processing mode 40 and a guarded processing mode 42 on the basis of rhythm and without regard to rate. Processor 28 effectively classifies and monitors and/or delivers therapy for non-benign rhythms at all rates.

Figure 5:
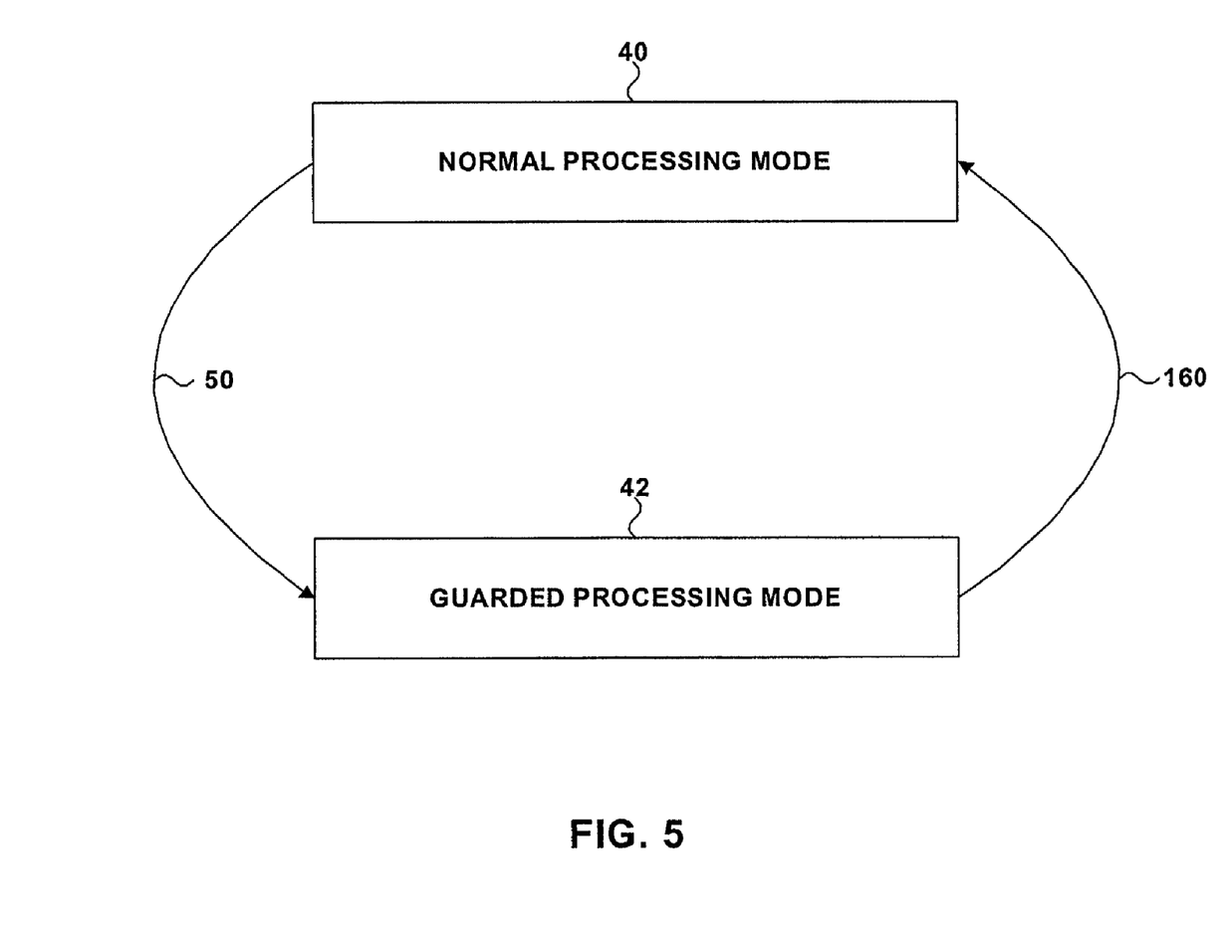
FIG. 5 is a state diagram illustrating an alternate implementation of the normal processing mode and the guarded processing mode.

FIG. 5 is a state diagram of another exemplary embodiment of the invention. Like FIG. 2, processor 28 may operate in a normal processing mode 40 and a guarded processing mode 42. Unlike the process shown in FIG. 2, which distinguishes between monitored processing zone 44 and ventricular therapy processing zone 46 in guarded processing mode 42, there is no such distinction in the process of FIG. 5. The invention is not limited to devices having a distinct monitored processing zone and ventricular therapy processing zone. When processor 28 is in guarded processing mode 42, processor 28 provides either monitoring or therapy, depending on the rhythm. Non-benign rhythms that are classified in guarded processing mode 42 as non-life threatening may be monitored whereas rhythms that are classified as VT, VF, or dual tachycardia may receive therapy.

Figure 6:
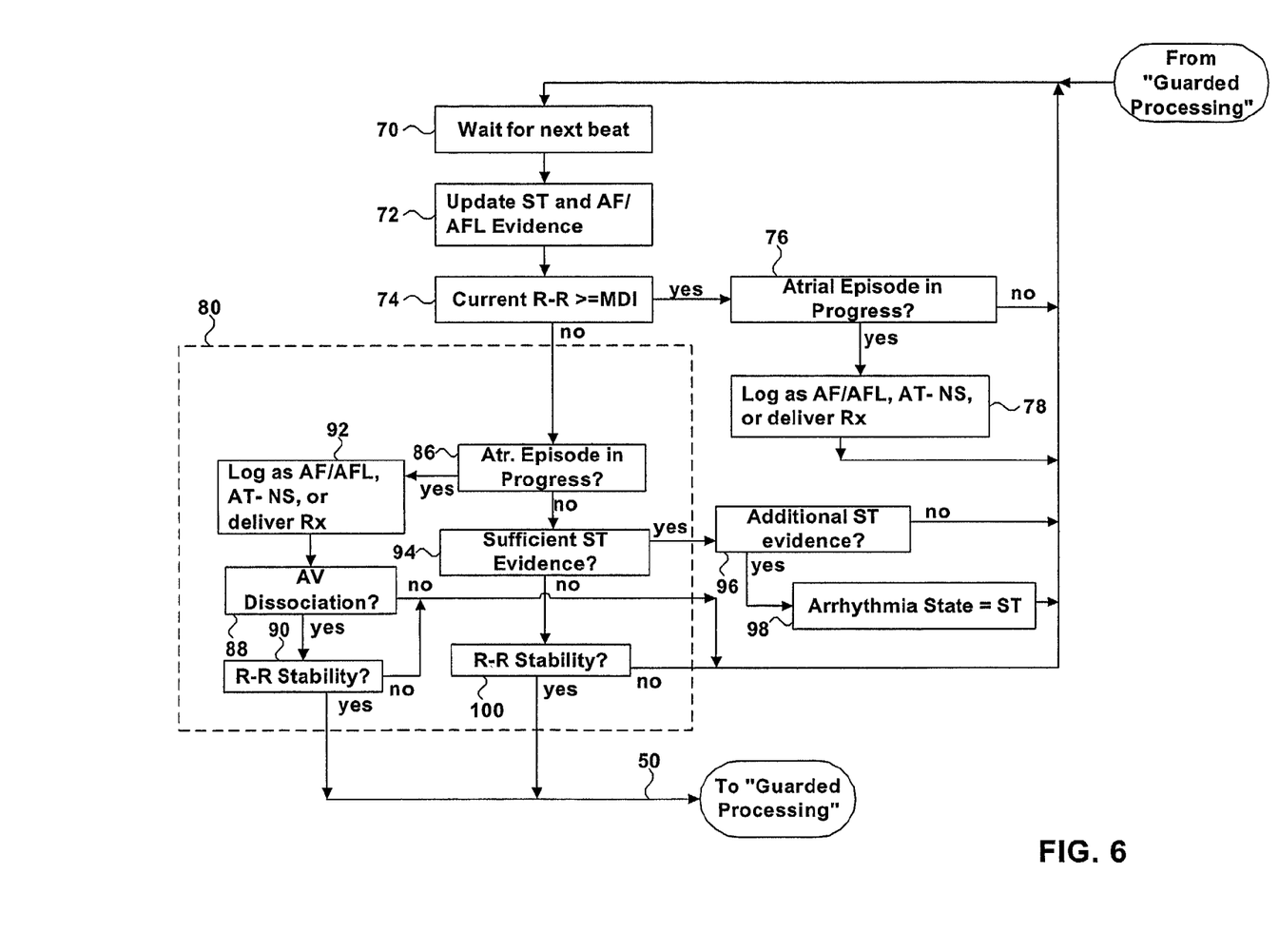
FIG. 6 is a flow diagram illustrating an alternate implementation of processing in the normal processing mode.

Normal processing mode 40 in FIG. 5 may be substantially the same as shown in FIG. 3, or normal processing mode 40 may employ an alternate computational analysis. FIG. 6 is a flow diagram illustrating an example of an alternate computational analysis by processor 28 in normal processing mode 40. FIG. 6 is similar to FIG. 3, but there is no comparison of the patient's rate to a threshold programmed by a physician (82 in FIG. 3), such as a TDI or FDI. Processor 28 makes a transition 50 to guarded processing mode 42 exclusively as a function of the patient's rhythm, rather than the patient's rate.

Figure 7:
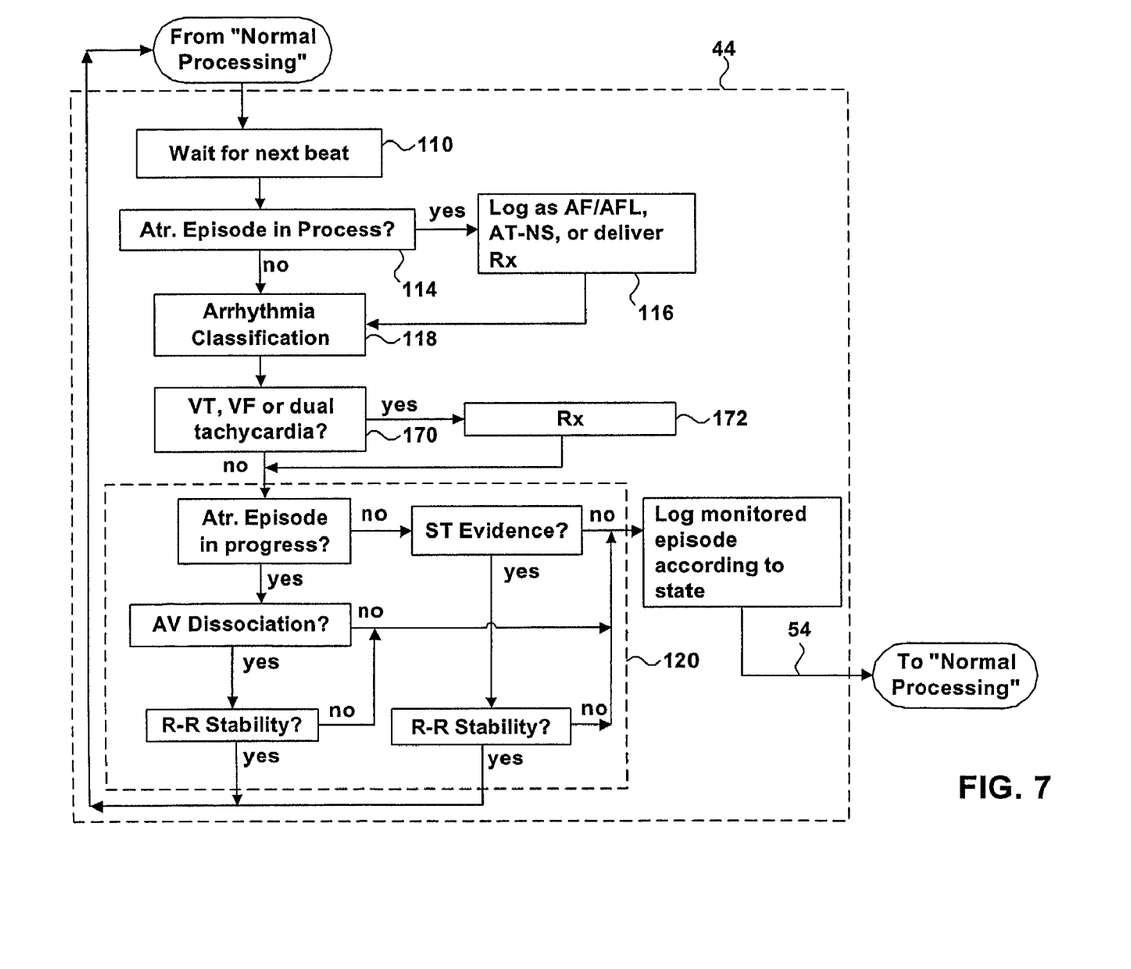
FIG. 7 is a flow diagram illustrating monitoring in a guarded processing mode.

FIG. 7 is a flow diagram illustrating an example of computational analysis by processor 28 in guarded processing mode 42. FIG. 7 is similar to FIG. 4, but there is no NID threshold (112 in FIG. 4). Rather, processor 28 classifies the rhythm (118) and delivers therapy when ventricular tachycardia, ventricular fibrillation or dual tachycardia are present (170, 172). Processor 28 performs an analysis to determine whether to remain in guarded processing mode 42 or whether to transition to normal processing mode 40 (124). In addition, the computational analysis of FIG. 7 does not compare the patient's rate to a threshold programmed by a physician (122 in FIG. 4). Processor 28 remains in guarded processing mode 42 as a function of the patient's rhythm, rather than the patient's rate.

In the exemplary embodiments of FIGS. 6 and 7, processor 28 performs computations based upon rhythm but without regard to rate. It is therefore unnecessary for a patient's physician to specify rate-based threshold intervals such as TDI or FDI. As a result, the physician need not be concerned about selecting an inappropriate threshold interval. Furthermore, processor 28 advantageously monitors and/or treats all rates. Processor 28 remains in normal processing mode 40 for benign rhythms and makes a transition to guarded processing mode 42 for rhythms that are not benign.

Maintaining a separate monitored processing zone 44 and ventricular therapy processing zone 46, such as are shown in FIG. 4, is not required for all patients, but may be advantageous for some patients. Separate zones 44, 46 may be advantageous, for example, when a single implanted device is used to pace the patient's heart and to provide arrhythmia therapy. In the ventricular therapy processing zone 46, tachyarrhythmia therapy and bradycardia pacing are incompatible in some implementations of the invention. In the monitored processing zone 44 shown in FIG. 4, however, there is no tachyarrhythmia therapy, and bradycardia pacing may be provided.

The exemplary embodiments described above perform classification computations when needed. When the rhythm is slow and benign, classification computations are not needed. When the rhythm is non-benign, however, classification computations are performed, even if the rhythm is comparatively slow. The implanted medical device is therefore able to respond to potentially harmful arrhythmias at all rates. An additional advantage of performing classification computations when needed is that the battery life of the implanted medical device may be extended. Various embodiments of the invention have been described. These and other embodiments are within the scope of the following claims.

The invention claimed is:

1. A method comprising:
   operating a processor in a low energy normal processing mode;
   receiving data indicative of a cardiac rhythm;
   determining if the cardiac rhythm is benign or non-benign based on a first algorithmic set;
   remaining in the normal processing mode if the rhythm is benign
   switching operation of the processor to a high energy guarded processing mode if the determined cardiac rhythm is non-benign and executing a second algorithmic set including a discriminatory arrhythmia classification algorithm to further classify the non-benign rhythm during operation in the guarded processing mode;
   switching to the normal processing mode when a benign rhythm returns.

2. The method of claim 1, further comprising operating the processor in the normal processing mode without regard to heart rate.

3. The method of claim 1, further comprising operating the processor in the guarded processing mode without regard to heart rate.

4. The method of claim 1, wherein operating the processor in the guarded processing mode in response to a non-benign heart rhythm comprises operating the processor in the guarded processing mode in response to evidence of one of atrial fibrillation and atrial flutter with atrioventricular dissociation and R-R interval stability.

5. The method of claim 4, wherein the evidence of one of atrial fibrillation and atrial flutter is a function of timing of P-waves and R-waves.

6. The method of claim 1, wherein operating the processor in the guarded processing mode in response to a non-benign heart rhythm comprises operating the processor in the guarded processing mode in response to insufficient evidence of atrial fibrillation and atrial flutter and sinus tachycardia, and in response to sufficient evidence of R-R interval stability.

7. The method of claim 6, wherein the evidence of atrial fibrillation and atrial flutter and sinus tachycardia is a function of timing of P-waves and R-waves.

8. The method of claim 1, further comprising operating the processor in the normal processing mode in response to a benign heart rhythm.

9. The method of claim 8, wherein the benign rhythm comprises at least one of a normal sinus rhythm, sinus tachycardia, atrial fibrillation, atrial flutter, 1:1 supraventricular tachycardia, a paced rhythm, bigeminy and non-sustained ectopy.

10. The method of claim 1, further comprising maintaining the processor in the normal processing mode in response to a benign heart rhythm.

11. The method at claim 1, wherein operating the processor in the guarded processing mode comprises operating the processor in one of a monitoring zone and a therapy zone, wherein operating the processor in the monitoring zone comprises monitoring the rhythm without delivery of therapy to the heart.

12. The method of claim 1, wherein the processor is included in an implanted cardiac monitoring device.

13. The method of claim 1, wherein the discriminatory arrhythmia classification algorithms comprise at least one of morphological analysis, operations on timing of P-waves and operations on timing of R-waves.

14. A computer-readable medium comprising instructions for causing a programmable processor to:
   operate a processor in a low energy normal processing mode;
   receive data indicative of a cardiac rhythm;
   determine if the cardiac rhythm is benign or non-benign based on a first algorithmic set;
   remain in the normal processing mode if the rhythm is benign switch operation of the processor to a high energy guarded processing mode if the determined cardiac rhythm is non-benign and executing a second algorithmic set including a discriminatory arrhythmia classification algorithm to further classify the non-benign rhythm during operation in the guarded processing mode;

switching to the normal processing mode when a benign rhythm returns.

15. The medium of claim 14, the instructions further causing the processor to operate the processor in the normal processing mode without regard to heart rate.

16. The medium of claim 14, the instructions further causing the processor to operate the processor in the guarded processing mode without regard to heart rate.

17. The medium of claim 14, wherein operating the processor in the guarded processing mode in response to a non-benign heart rhythm comprises operating the processor in the guarded processing mode in response to evidence of one of atrial fibrillation and atrial flutter with atrioventricular dissociation and R-R interval stability.

18. The medium of claim 17, wherein the evidence of one of atrial fibrillation and atrial flutter is a function of timing of P-waves and R-waves.

19. The medium of claim 14, wherein operating the processor in the guarded processing mode in response to a non-benign heart rhythm comprises operating the processor in the guarded processing mode in response to insufficient evidence of atrial fibrillation and atrial flutter and sinus tachycardia, and in response to sufficient evidence of R-R interval stability.

20. The medium of claim 19, wherein the evidence of atrial fibrillation and atrial flutter and sinus tachycardia is a function of timing of P-waves and R-waves.

21. The medium of claim 14, the instructions further causing the processor to operate the processor in the normal processing mode in response to a benign heart rhythm.

22. The medium of claim 21, wherein the benign rhythm comprises at least one of a normal sinus rhythm, sinus tachycardia, atrial fibrillation, atrial flutter, 1:1 supraventricular tachycardia, a paced rhythm, bigeminy and non-sustained ectopy.

23. The medium of claim 14, the instructions further causing the processor to maintain the processor in the normal processing mode in response to a benign heart rhythm.

24. The medium of claim 14, wherein operating the processor in the guarded processing mode comprises operating the processor in one of a monitoring zone and a therapy zone, wherein operating the processor in the monitoring zone comprises monitoring the rhythm without delivery of therapy to the heart.

25. The medium of claim 14, wherein the processor is included in an implanted cardiac monitoring device.

26. The medium of claim 14, wherein discriminatory arrhythmia classification algorithms comprise at least one of morphological analysis, operations on timing of P-waves and operations on timing of R-waves.

* * * * *